(12) United States Patent
Brohm-Schmitz-Rode (10) Patent No.: US 11,135,076 B2
(45) Date of Patent: Oct. 5, 2021

(54) TUBULAR SLEEVE AND SYSTEM FOR THE ATRAUMATIC TREATMENT OF HOLLOW ORGANS

(71) Applicant: BVS—Best Vascular Solutions GmbH, Bonn (DE)

(72) Inventor: Andrea Brohm-Schmitz-Rode, Aachen (DE)

(73) Assignee: BVS—Best Vascular Solutions GmbH, Bonn (DE)

( * ) Notice: Subject to any disclaimer, the term of this patent is extended or adjusted under 35 U.S.C. 154(b) by 314 days.

(21) Appl. No.: 15/561,522

(22) PCT Filed: Mar. 23, 2016

(86) PCT No.: PCT/EP2016/056429
§ 371 (c)(1),
(2) Date: Mar. 16, 2018

(87) PCT Pub. No.: WO2016/151035
PCT Pub. Date: Sep. 29, 2016

(65) Prior Publication Data
US 2019/0231565 A1    Aug. 1, 2019

(30) Foreign Application Priority Data
Mar. 23, 2015   (DE) .................. 10 2015 104 338.6

(51) Int. Cl.
*A61F 2/06*     (2013.01)
*A61F 2/945*    (2013.01)
(Continued)

(52) U.S. Cl.
CPC .............. *A61F 2/945* (2013.01); *A61F 2/844* (2013.01); *A61F 2/958* (2013.01); *A61F 2002/9583* (2013.01); *A61F 2210/0061* (2013.01)

(58) Field of Classification Search
CPC .... A61F 2/2418; A61F 2/2436; A61F 2/2457; A61F 5/0013; A61F 13/00038;
(Continued)

(56) References Cited

U.S. PATENT DOCUMENTS 5,507,770 A  *  4/1996  Turk ..................... A61F 2/07
                                                    606/198
6,059,823 A      5/2000  Holam et al.
(Continued)

FOREIGN PATENT DOCUMENTS

DE   10 2006 020 687 A1   2/2007
DE   10 2005 056 529 A1   5/2007
(Continued)

OTHER PUBLICATIONS

International Search Report (ISR) relating to International Application No. PCT/EP2016/056429, dated May 27, 2016.
(Continued)

*Primary Examiner* — Ann Schillinger (57) ABSTRACT

The invention relates to a tubular sleeve for the atraumatic treatment of hollow organs, wherein the sleeve is folded in an initial state and can be unfolded in order to lie against an inner wall of a hollow organ in a final state. The sleeve is characterized in that the sleeve is formed of an outer wall and an inner wall, which are arranged concentrically to each other, wherein the outer wall and the inner wall are tightly connected to each other at ends thereof in such a way that an approximately tubular compartment is formed in the region between the outer wall and the inner wall and the folding of the sleeve is directed about a sleeve longitudinal axis.

17 Claims, 6 Drawing Sheets

(51) Int. Cl.
*A61F 2/844* (2013.01)
*A61F 2/958* (2013.01)

(58) Field of Classification Search
CPC ...... A61F 13/00068; A61F 2002/30578; A61F 2002/30593; A61F 2002/30604; A61F 2/0027; A61F 2/004; A61F 2/04
See application file for complete search history.

(56) References Cited

U.S. PATENT DOCUMENTS

| | | | |
|---|---|---|---|
| 2002/0045930 A1 | 4/2002 | van der Burg et al. | |
| 2002/0187184 A1* | 12/2002 | Golomb | A61K 9/5153 424/450 |
| 2004/0137066 A1* | 7/2004 | Jayaraman | A61K 31/436 424/486 |
| 2005/0027348 A1* | 2/2005 | Case | A61F 2/2475 623/1.24 |
| 2005/0090888 A1 | 4/2005 | Hines et al. | |
| 2005/0125053 A1 | 6/2005 | Yachia et al. | |
| 2008/0262594 A1 | 10/2008 | Morris | |
| 2008/0281355 A1* | 11/2008 | Mayer | B29C 61/0608 606/228 |
| 2009/0112305 A1 | 4/2009 | Goldmann et al. | |
| 2009/0149941 A1 | 6/2009 | Hasson et al. | |
| 2010/0249946 A1 | 9/2010 | Lesh et al. | |
| 2014/0141152 A1* | 5/2014 | Sostek | D04H 1/4382 427/2.24 |

FOREIGN PATENT DOCUMENTS

| | | | |
|---|---|---|---|
| WO | WO 9610967 | 4/1996 | |
| WO | WO-9610967 A1 * | 4/1996 | ............... A61F 2/82 |

OTHER PUBLICATIONS

Written Opinion of the ISA relating to International Application No. PCT/EP2016/056429, dated May 27, 2016.

* cited by examiner

TUBULAR SLEEVE AND SYSTEM FOR THE ATRAUMATIC TREATMENT OF HOLLOW ORGANS

CROSS REFERENCE TO PRIOR APPLICATION

This application is a National Stage Patent Application of PCT International Patent Application Ser. No. PCT/EP2016/056429 (filed on Mar. 23, 2016) under 35 U.S.C. § 371, which claims priority to European Patent Application Ser. No. DE10 2015 104 338.6 (filed on Mar. 23, 2015), which are all hereby incorporated by reference in their entireties.

The present invention relates to a tubular sleeve and a system for the atraumatic treatment of hollow organs.

For treatment of narrowings (stenoses) in human hollow organs, such as, for example, in blood vessels, stents are known. A stent (vascular support device) is a medical implant that can be inserted into a hollow organ. It is usually a tubular framework made of metal or plastic. The stent is intended to support the affected section of a hollow organ and in this way permanently hold it open.

Usually, stents are delivered to the implantation site by means of a catheter or balloon catheter. For this purpose, the stent is placed on a balloon catheter. The stent is intended to have an outer diameter as small as possible in order to damage the corresponding hollow organ as little as possible when inserted into the human and/or animal body. For this purpose, radial crimping forces are mostly applied to the stent so that a concentric diameter reduction takes place. If the stent is placed at the implantation site, the balloon catheter is inflated so that a concentric expansion of the stent occurs.

In some cases the stent material may cause clot formation (thrombogenicity). Furthermore, the mechanical stress during the inflation of the balloon catheter can lead to an injury to the vessel wall of the hollow organ. In the long term, the stent often leads to chronic irritation. The vessel wall reacts to this irritation with an overproduction of wall cells and so-called extracellular matrix (hyperplasia). Such a vessel wall proliferation can be so strongly pronounced that a reconstriction of the blood vessel (restenosis) occurs. Due to the thrombogenicity of the dilatation cracks in the vessel wall and also of the stent material, a medicinal anticoagulation treatment is often carried out, which should prevent clot formation. However, this therapy may have side effects. Therefore, a reduction in medication would be desirable.

Furthermore, it is frequently attempted to reduce the vessel wall proliferation by so-called "drug eluting stents". In general, such stents are coated with a polymer into which antiproliferative active substances are incorporated or the stents are doped otherwise with such active substances. The release of the active substances at the implant site reduces the overproduction of wall cells. However, in some patients, these agents prevent ingrowth of the stent into the wall of the vessel. After termination of the anticoagulation medication there may occur so-called late thromboses, because the stent is not at all or not fully grown into the vessel wall.

In order to avoid the above problems, new stent concepts are followed, including so-called bioresorbable stents. These can be made from biodegradable metal alloys, for example with a high magnesium content, or from biodegradable polymers, for example polylactide. In this case, it is envisaged that such stents support the vessel wall for a few months and subsequently biodegrade by means of natural degradation processes. In this way, the mechanical irritation on the vessel wall should be reduced and there should be less restenosis development. However, according to first clinical studies, it is not possible to dispense with antiproliferative drugs in the case of biodegradable stents, because the proliferative vessel wall reaction has to be suppressed in the first months after implantation.

A stent and a stent implantation catheter are disclosed in DE 10 2012 007 640. A stent body of this stent is intended in particular to have an inner wall formed from an expandable material in such a way that a closed surface is formed after the implantation. The closed surface is intended to act as a kind of wound closure. According to a further embodiment, the stent body is intended to have a wall of expandable material both on the inside and on the outside. The material is directly or indirectly connected to the stent body. Therefore, the expansion of the material occurs together with the stent body. Accordingly, the stent body and the walls are expanded by a concentric diameter expansion.

In the case of a stent implantation, diameters are typically increased by a factor of 1:3 or 1:4. This means an increase of the circumference by a factor of 18 to 24. Therefore, such walls connected to the stent should feature a high plastic stretchability of the material. However, this is a major challenge from the point of view of materials engineering.

WO 02 076 700 A1 discloses a balloon catheter. The material forming the balloon catheter is thereby pleated and folded, the material being firmly connected to a catheter shaft.

An angioplasty balloon implant device is disclosed in U.S. Pat. No. 5,443,495 A1. In this case, it is provided that, after inflation of a balloon catheter, a part of the balloon wall can be detached from the balloon catheter. This is to be done by the expansion force released during the expansion of the balloon catheter, wherein predetermined breaking points are provided in order to detach end segments of the balloon film which are fixedly connected to the catheter shaft. The balloon film therewith is an integral part of the balloon catheter. Furthermore, it is also possible to provide a polymer stent on the balloon catheter.

Stents commonly used today, even with particularly miniaturized designs, for example, for cerebral arteries or peripheral coronary arteries, have a diameter of 1.5 mm to 2.5 mm in the expanded state. In the expanded state, the mesh openings, i.e. the maximum distances between the expanded stent struts, show a width of more than 150 µm.

In the case of stents, which are expanded by balloon catheters, the diameter widening occurs due to a plastic deformation of the stent struts, in particular in the connecting points connecting the stent struts. There is therefore a plastic deformation of the stent material. However, in this case almost always a contraction or a recoil of the stent occurs, which can lead to a first re-constriction of the treated hollow organ. Responsible for this tendency to recoil are usually restoring forces in the stent material, such as nitinol.

A stent-graft prosthesis is disclosed in DE 10 2006 020 687 A1. This stent-graft prosthesis comprises a flexible sheath for the lining of an aneurysm and may have an aortic insert associated with the sheath in the form of a vascular prosthesis with expandable support structures. Furthermore, the sheath and the aortic insert can be sealingly connected to one another at their proximal and distal ends in such a way that a chamber is formed. The outer sheath is oversized such that pleats are formed transverse to the longitudinal direction of the sheath within the aneurysm.

A pleated stent device is disclosed in US 2005/0 090 888 A1. The stent is placed in a pleated condition on a balloon to form a pleated balloon assembly.

A compressible tissue support is disclosed in DE 2005 056 529 A1. This approximately tubular shaped tissue support is formed from a shape memory material, the tissue support being folded one or more times in its longitudinal axis.

US Pat. No. 2002/0 045 930 A1 discloses a stentgraft unfolding device and a corresponding method. The stentgraft itself is folded along its longitudinal axis. Furthermore, the tubular stent can be reinforced by means of fibers which are embedded either in the tubular stentgraft or are arranged coaxially on the tubular stentgraft in a separate layer.

US 2005/0 125 053 A1 discloses a tubular medical device, such as a stent or a catheter. This has a plurality of rows of slots, the device being designed to be collapsible to a smaller diameter.

US Pat. No. 2008/0 262 594 A1 describes a stentgraft sealing system and a corresponding method. In this case, an inner tubular body is provided which is pleated about its longitudinal axis, a stent being arranged on the inner body. The tubular graft material may be connected to a sealing stent at its outer folds.

The object of the present invention is to provide a medical instrument for the atraumatic treatment of hollow organs, which is an alternative to the medical devices known from the prior art, for example, stents, and which offers broader application possibilities.

A further object of the present invention is to provide an improved medical instrument for the atraumatic treatment of hollow organs.

These objects are achieved with a device according to claim 1. Advantageous embodiments thereof are given in the subclaims.

According to the invention, a tubular sleeve is provided for the atraumatic treatment of hollow organs, wherein the sleeve is folded in an initial state and can be unfolded in an end state to an inner wall of a hollow organ.

The sleeve is characterized in that the sleeve is formed from an outer wall and an inner wall, which are arranged concentrically to one another, the outer wall and the inner wall being connected to one another on the end faces so tightly that in the region between the outer wall and the inner wall form an approximately tubular compartment, and the folding pleats of the sleeve are oriented along a longitudinal axis of the sleeve.

In the compartment, one or more fillers can be arranged for various medical applications and/or for improving mechanical properties. Various types of fillers suitable for assembly in the compartment are described in detail below.

Due to the fact that the folding of the sleeve is orientated along the longitudinal axis of the sleeve, it is possible to provide a tubular sleeve in which the initial diameter in the folded state is extremely small. This allows a relatively simple and safe insertion of the sleeve in the folded state to the implantation location because of the small outer diameter. In particular, it is provided that both the inner wall and the outer wall are folded in the same folding pattern. Furthermore, the initial diameter of the folded tubular sleeve is substantially smaller than the outer diameter required at the implantation site after the deployment (unfolding) of the sleeve.

For the purposes of the present invention, the compartment of the tubular sleeve may comprise a single compartment or else a plurality of compartments or else a plurality of (to multiple) micro-compartments.

Within the scope of the present invention, an approximately tubular compartment is defined as a space which is limited by the inner and outer walls. The shape of this space is not limited to a cylindrical ring shape, but the thickness of the compartment can vary both in the longitudinal direction of the tubular sleeve and transversely to the longitudinal direction and can be interrupted by walls, webs or the like.

The tubular sleeve can have a lattice-like circumferential surface. This means that defects (spaces) can be formed in the outer and inner wall. Nevertheless, the individual lattice struts of such a latticed wall of the sleeve also have at least one or more compartments.

The tubular sleeve can have a closed circumferential surface. This means that the sleeve has a continuous, closed outer surface in which there are no imperfections. The outer wall and/or the inner wall or an inner and an outer circumferential surface of the sleeve can be designed essentially closed.

In the context of the present invention, a closed circumferential surface is understood to be a wall which can be completely closed or pore-free or has a low porosity, the pores formed in the sleeve having a diameter of less than 100 µm or less than 80 µm, or less than 60 µm, or less than 40 µm, or less than 30 µm, or less than 10 µm, and preferably less than 20 µm. The values indicated can also refer to a maximum pore width of an elliptical or differently shaped pore, the values then being the widest width of the pore opening.

With such a pore size, it is prevented that blood corpuscles, such as platelets (thrombocytes), enter the sleeve, which alleviates some of the above-described disadvantages, in particular the thrombogenicity, i.e., the tendency to blood clot formation, in the region of the treated vascular lesion. By completely covering the lesion through the sleeve, the interaction with blood and blood corpuscles, which would otherwise take place continuously, is avoided. This refers in particular to the attachment and activation of blood corpuscles. In particular, the activation of blood platelets and thus the activation of the coagulation system is reduced.

At the indicated values it may be possible that a few blood corpuscles enter and/or remain in the pores. Nevertheless, the activation of blood platelets and the coagulation system is significantly reduced because there is no continuous interaction with new blood platelets.

One or both walls of the lattice-like sleeve can likewise have a substantially closed circumferential surface and accordingly pores.

The sleeve according to the invention can be arranged on a balloon catheter. The sleeve is then delivered to the implantation site together with the balloon catheter. By expansion of the balloon catheter, the sleeve is unfolded and forms a closed tubular covering of the balloon-dilated, previously constricted or obstructed hollow organ.

Because the sleeve can be arranged in a folded state on a balloon catheter, it has a small outer diameter, when penetrating into the human body. The outer diameter or the circumference is correspondingly increased by unfolding at the implantation site. However, the folding does not require a larger plastic stretching of the sleeve material. Thus, in the case of the sleeve according to the invention, in contrast to balloon-expandable stents, it also does not result in the formation of restoring forces, which lead to a rebound to a smaller diameter (recoil). Such a recoil of dilated stents leads to a first re-narrowing of the treated lesion.

As already described above, it is provided according to the invention that the outer diameter of the tubular sleeve, after unfolding, approximately corresponds to the diameter of an inner wall of a hollow organ.

Ruptures in the wall of the hollow organ, which have been caused by the expansion or inflation of the balloon catheter, are excluded from the direct contact with blood by the unfolded sleeve which completely covers the lesion. In this way, the thrombogenicity, i.e. the tendency of blood clot formation, is reduced in the region of the treated vascular lesion.

Preferably, the folding of the tubular sleeve can be designed as pleating or the sleeve can be pleated. In the context of the present invention, pleating is understood to mean the pleating and pressing of the tubular sleeve. As a result of the pleating, it is possible to reduce the outer diameter of the tubular sleeve in the non-unfolded state. Optionally, an adhesive may be applied to the folded sleeve to stabilize the pleating and thereby maintain the small diameter during transport to the implantation site.

The folding of the sleeve is directed about a sleeve longitudinal axis, whereby the folding can take place both in the clockwise and in the counterclockwise direction. Folding and pleating are carried out similarly to the principle described in WO 02 076 700 A1 by means of a balloon catheter.

The tubular sleeve may also be provided with a medicinal active agent, such as, for example a hydrogel layer. The hydrogel layer preferably has a thickness of approximately 5 µm to 20 µm, and of 7.5 to 12.5 µm, in particular of 10 µm. The hydrogel layer is loaded, for example with an antiproliferative, e.g. paclitaxel or everolimus.

By doping the outer surface of the sleeve with a hydrogel layer, the sleeve adheres to an inner wall of a hollow organ, in particular a blood vessel, due to the hydrogel layer, after deployment.

In addition, a biocompatible adhesive such as, for example a hydrogel, can stabilize the pleated state of the sleeve during transportation to the implantation site.

The sleeve can be formed from a film or a textile structure. Suitable materials are, for example, biocompatible plastics, in particular biodegradable polymers such as the polylactides.

The textile structure can be woven, knitted, braided and/or lace-made, or formed from a nonwoven.

A nonwoven is a structure of fibers of limited length, endless fibers (filaments), or cut yarns of any kind and any origin, which have been joined in some way to a nonwoven (a fiber layer, a fiber web) and joined together in some manner.

Nonwovens are for the most part flexible laminar textile fabrics, that is to say they are easily flexible, their main structural elements are textile fibers and they have a comparatively small thickness in relation to their length and width. There are also nonwovens which, because of the fibers applied or their consolidation methods used, are more similar to papers, films or fiber-reinforced plastics than textiles. Nonwovens are a material group with a wide range of properties that can be adapted to a wide range of medical application requirements.

The textile structure can also be achieved by means of entangling of yarns, such as occurs during weaving, knitting, lace making, braiding and production of tufted products.

In an embodiment of the sleeve wall from a nonwoven, multiple polymorphic micro-compartments are formed, which have a capillary suction effect and thus can suck passively a liquid binder (or blood plasma)—and thus provoke in-situ crosslinking.

Furthermore, the sleeve can be cylindrical. Alternatively, the sleeve can also have any shape known from the stent area. That means, the sleeve may be conical, branched, pinched (like an egg timer), elliptical or circular in a side view.

The material from which the sleeve is formed and its coating preferably have a certain conformability in order to adapt to the structure of a wall or the surface structure of a hollow organ, in this way covering lesions.

In addition, the material preferably has a low elasticity, that is to say it is elastically deformable only within certain limits in order to prevent a recoil with a certain strength in the case of an embodiment of the tubular sleeve described below.

Nanoparticles or textile fibers or a nonwoven can be arranged as filler in the compartment. Furthermore, a sticky, pasty mass can be arranged in the compartment as a filler.

Accordingly, both the outer wall and the inner wall and the filler can be formed from a nonwoven, preferably from one and the same nonwoven or else from two different nonwoven fabrics. An outer surface of the nonwoven then forms the outer wall, and an inner surface of the nonwoven then forms the inner wall of the tubular sleeve.

The interspaces between textile fibers of the nonwoven fabric then constitute micro-compartments for the purposes of the present invention. In these micro-compartments, a filler, such as, for example, a binder, can be arranged or it is possible for blood plasma to enter the micro-compartments and act as a binder.

The thickness of the outer wall and of the inner wall can each be approximately 20 µm to 30 µm. The thickness of the compartment transversely to the longitudinal direction, respectively in the radial direction, can also be approximately 20 µm to 30 µm.

Furthermore, the closed tubular compartment may be divided into two or more or multiple sub-compartments filled with different components, for example with a prepolymer or polymer (textile fibers, particles, powder or nonwoven), and with a crosslinking agent or adhesive.

In this case, it is provided that the spatial separation of the different components by the sub-compartments is canceled by expansion of the balloon catheter by destroying separating structures, so that the different components come into contact with each other. In this way, a mechanical consolidation or a chemical crosslinking reaction takes place, which imparts a mechanical strength to the deployed sleeve.

Between the inner wall and the outer wall, an intermediate wall can be provided in such a way that two coaxially extending compartments are formed. In principle, two or more intermediate walls are also possible, so that a plurality of coaxially extending compartments are formed.

In such an embodiment, wherein the intermediate wall has a smaller deployment diameter than the inner and outer walls, the intermediate wall is ruptured by the balloon pressure. In this way, a connection is then established between the two compartments.

Between the inner wall and the outer wall, an intermediate wall can be provided in such a way that two compartments arranged one behind the other in the longitudinal direction are formed. In principle, two or more intermediate walls are also possible so that a plurality of compartments arranged one behind the other in the longitudinal direction are formed.

The walls of the sleeve can be connected to one another by connecting points or lines, which are produced, for example, by gluing or welding.

Such connecting points or lines bring about a better cohesion between the walls during the pleating, folding and unfolding process. The connecting points or lines can be formed as a pattern of connecting points arranged on the sleeve surface, for example by laser welding.

The sleeve or at least one of the compartments can have a supply channel, via which a liquid component can be fed from the outside to the compartment.

In the unfolding state of the sleeve, an in situ polymerization of at least two components can take place in one or more of the closed tubular-shaped compartments.

Such in-situ polymerization results in mechanical stabilization of the deployed sleeve, which prevents collapse into the folded state. The polymerization should be possible at a balloon pressure of up to 25 atm and do not exceed reaction times of 10 to 15 seconds.

The polymerization can be effected by:
- a mechanical assembly of the components (e.g. PLA powder or PLA microspheres 1-2 μm and binders, respectively crosslinkers) by penetration of partition walls between the compartments, or
- a fluid mechanical active injection or a passive suction of a liquid cross-linking agent, or
- a mechanical and thermal action of ultrasound, or
- an optical-thermal load, or
- a thermal load, or
- a chemical reaction, for example by so-called click chemistry, such as the thiol-ene reaction.

For example, an ultrasonic probe can be integrated into the balloon catheter or can be fed to it for a mechanical and thermal action by means of ultrasound.

An optical-thermal loading can be effected, for example, by means of a laser which can be integrated into the balloon catheter or can be fed to it. By the action of UV light (approx. 275 nm) on the corresponding component, a laser sintering of PLA powder can take place.

A thermal application can be effected, for example, by means of a high-frequency probe, which can be integrated into the balloon catheter or can be fed to it.

A chemical reaction, for example, by so-called click chemistry, such as the thiol-ene reaction, can be effected, for example, by photo-polymerization and integration of a UV laser into the balloon catheter.

The walls of the sleeve can be connected to one another, for example by means of laser welding, in that channels are formed which form a pattern, for example, a diamond pattern. This pattern can be designed in such a way that strut-shaped channels are formed which are similar to the struts of a stent.

The channels or the compartments or the sub-compartments or the interspaces can be filled with a crosslinkable polymer component or a component that can be mechanically consolidated under balloon pressure.

The channels or the compartments or the sub-compartments can be filled with a filler, in particular a dry substance, for example a polymer nanopowder, whereas the interstices between the powder being filled with a liquid crosslinking agent or a liquid binder.

In this case, it is provided that the components come into contact with one another as soon as the spatial separation of the components is canceled by expansion of the balloon catheter since the corresponding partition walls are destroyed.

The outer surface of the sleeve may be coated with a medical agent such as, for example, an antiproliferative, and/or a healing-promoting substance, such as, for example, fibrin gel, which may optionally be mixed with autologous cells of the patient.

Furthermore, a doping of the inner surface of the sleeve with an antithrombogenic substance such as, for example, heparin, and/or an active substance, which promotes endothelial cell coating.

In addition, pretreatment or priming of the inner and outer surface of the sleeve can be effected immediately before the implantation in that the surface is treated with body-specific substances of the recipient patient (e.g. full blood, plasma, serum, cells).

A wetting of the inner and/or outer surface of the sleeve during the implantation process ("in situ") with bioactive substances or body's own (autologous) substances of the recipient patient is likewise possible by injecting them via corresponding supply channels via one or more compartments which are connected to openings of the inner and/or outer surfaces of the sleeve.

The adhesion of the substances can be improved by surface structuring or gel film deposition of the surfaces of the sleeve.

In particular, according to the invention, a system for the atraumatic treatment of hollow organs is provided, which comprises a balloon catheter and a tubular sleeve.

In addition, in this system, an outer protective sheath can be arranged on the sleeve in the initial (folded) state.

By such a foil-like protective sheath, blood contact is avoided and thus thrombus formation during the introduction of the sleeve is prevented. At the implantation site, the protective sheath can then be removed by retraction or by a deployment-induced tearing. Moreover, the stability of the folding of the sleeve for transport on the balloon catheter can be assisted by an adhesive surface treatment of the outer surface of the sleeve.

The sleeve according to the invention comprises a structured wall design with compartmentalization. This means that at least one compartment is provided, or a plurality of compartments separated from one another by walls or webs or microcompartments are provided. A compartment in the sense of the present invention is thus a defined space which can be filled with a filler such as, for example, a liquid, a powder and/or a gel.

The sleeve may further comprise a closed or a porous circumferential surface, with connection points and lines being provided between the inner and outer surfaces of the sleeve. The sleeve can also be designed as a lattice structure with a circumferential surface with or without pores.

The invention is described in more detail below with reference to the exemplary embodiments shown in the figures.

Figure 1:
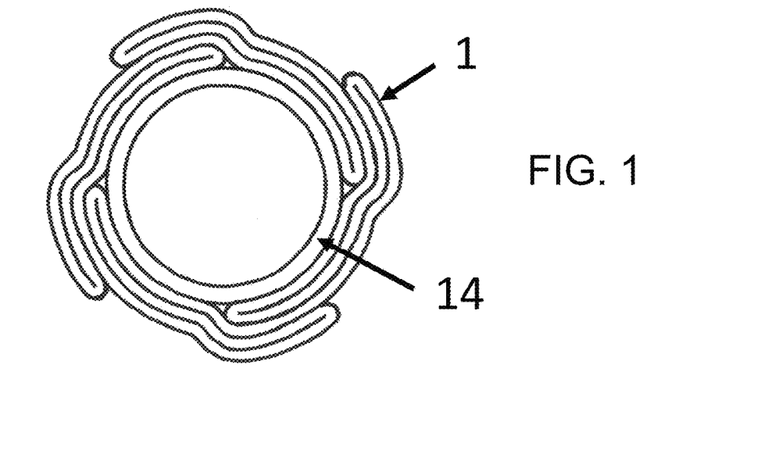
FIG. 1 shows a pleated and folded sleeve in a plan view from the front according to a first embodiment of the device according to the invention.

The tubular sleeve 1, respectively its wall 3, is pleated and folded in an initial state. The folding of the sleeve is orientated along longitudinal axis of the sleeve 2. Furthermore, the folding takes place clockwise or counterclockwise about the longitudinal axis 2 of the sleeve.

The wall is made of a film, for example made of polylactide (PLA). The film has a thickness of approximately 20 μm to 90 μm, and of approximately 40 μm to 70 μm, in particular 50 μm.

Furthermore, the outer wall or the jacket wall 3 is coated with a highly pasty hydrogel in such a way that a hydrogel layer 4 is covering the entire surface of the wall 3. The hydrogel layer 4 preferably has a thickness of approximately 10 μm to 50 μm and is loaded or doped, for example, with an antiproliferative, e.g. paclitaxel or everolimus. A preferred doping range for everolimus is 7 μg/mm to 10 μg/mm in a 1:1 mixture with the hydrogel matrix.

In the embodiment of the sleeve, in which the circumferential wall is formed only from a single-layer film, a thicker hydrogel layer with a thickness of, for example 40 μm, is provided, in order to compensate for irregularities of an inner vessel wall and to enlarge the contact surface area. In the case of multilayer walls, the thickness may be about 10 μm to 30 μm or about 15 μm to 20 μm.

Figure 3:
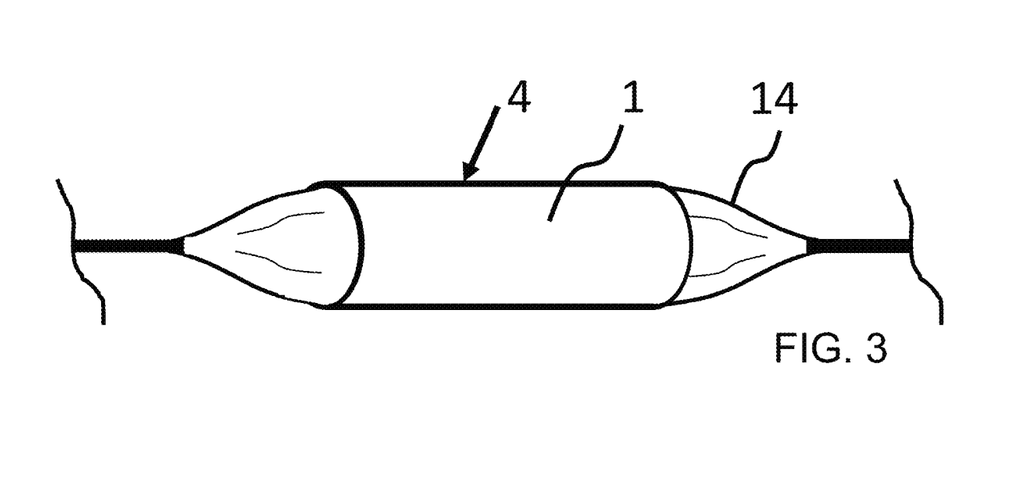
FIG. 3 shows a perspective side view of the sleeve according to the invention on a balloon catheter with an inflated balloon.

The tubular sleeve is placed in a pleated and folded initial condition on a collapsed balloon catheter 14. After being folded on a removable core the sleeve can be slipped over the folded balloon of a balloon catheter. Alternatively, folding may be performed directly on the balloon catheter with the balloon catheter balloon already in a folded condition. Alternatively, it is also possible to pleat and fold the balloon film and the sleeve together in one working step. This procedure promotes the cohesion between the balloon film and the sleeve during transport to the implantation site of the sleeve. In all cases, the pleating and folding of the pleats of the sleeve can be supported by application of an adhesive in order to stabilize the folded sleeve for the phase of the transport to the implantation site. However, only a slight adhesive bond between the balloon catheter and the sleeve should be provided to allow the sleeve to readily detach from the surface of the balloon within the deflation process, following inflating the balloon catheter. The initial diameter of the folded tubular sleeve is substantially smaller than the outer diameter required at the implantation site after the deployment (unfolding) of the sleeve 1.

The stability of the folding and pleating of the sleeve 1 during transport or insertion into the hollow organ can be supported by an adhesive surface treatment of the outer wall of the sleeve.

At the implantation site, the tubular sleeve 1 is unfolded in its final state by the expansion of the balloon catheter 14 in such a way, that the sleeve 1 is unfolded and unpleated.

Figure 2:
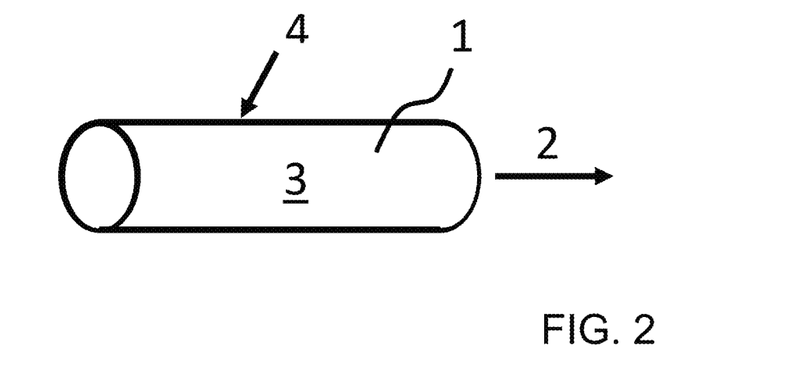
FIG. 2 shows a perspective view from the side of the sleeve according to the invention in the unfolded state.

The cylindrical wall 3 is pressed from the inside against the affected wall segment of an inner wall of a hollow organ. Due to the adhesive property of the hydrogel layer 4, the tubular sleeve 1 adheres independently to the inner wall of the hollow organ, in particular of a blood vessel. Due to the pleating a larger plastic distension of the sleeve material is not necessary. Thus, in the case of the inventive sleeve 1, unlike balloon-expandable stents, there is also no recoil. The sleeve is deployed only by the inflation of the balloon to an end diameter, which essentially corresponds to the inner diameter of the affected vessel wall. The sleeve 1 is then aligned to the vessel wall as a thin-walled tubular implant.

By means of the sleeve, which completely covers the lesion, cracks in the blood vessel wall, which are caused by the balloon expansion, are excluded from direct contact with blood.

In this way, the thrombogenicity or the tendency to form blood clots in the region of the treated vessel lesion is reduced.

In particular, it is provided that the active substance embedded in the hydrogel, depending on the dosage and type of embedding in the hydrogel, acts on the vessel wall for an extended period of approximately three to five months in such a way that the reactive proliferation of vessel wall cells (as a reaction to the trauma) is reduced.

If the sleeve is made of polylactide, it is degraded after a certain period of time, preferably after three to five months.

During the deflation of the balloon catheter, the sleeve detaches itself from the balloon outer surface and then adheres to an inner wall of the hollow organ, for example the blood vessel wall, as a thin-walled tubular implant.

Alternatively, the sleeve may be formed from a thin-walled, textile structure. Such a structure may be woven, knitted, braided or lace-made. In addition, an embodiment of a tubular nonwoven is also possible.

Figure 4:
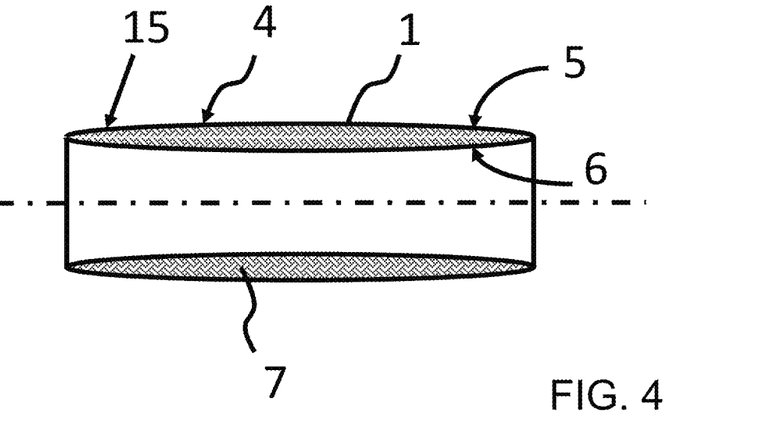
FIG. 4 shows a further embodiment of a sleeve according to the invention in a sectional side view.

According to one embodiment of the present invention, the tubular sleeve 1 is formed from two concentrically arranged cylindrical walls, the outer wall forming an outer circumferential surface 5 and the inner wall forming an inner circumferential surface 6 (FIG. 4).

Unless otherwise described, this embodiment corresponds to the embodiment described above.

In this case, it is provided that end regions or, respectively, front and rear end faces of the outer wall 5 and the inner wall 6, which are located in the longitudinal direction 2 of the sleeve 1, are tightly connected to one another, for example by means of welding. A one-piece connection of the outer wall 5 and the inner wall 6 is also possible.

In this way, a closed, essentially tube-shaped compartment 7 is formed in the region between the outer wall 5 and the inner wall 6 (FIG. 4). The outer wall 5 and the inner wall 6 are likewise, as already described above, preferably made of a film, e.g. made of polylactide (PLA).

The thickness of the outer wall 5 and the inner wall 6 is in each case approximately 20 μm to 30 μm. The thickness of the compartment 7 transversely to the longitudinal direction or in the radial direction 2 is also approximately 20 μm to 30 μm.

A thin layer of a biocompatible substance is arranged in compartment 7. The substance can be a mixture of polylactide nanomicrofibers with a fiber diameter of 100 nm and a fiber length of 2 μm to 5 μm and an adhesive or binder, such as, for example a highly viscous hydrogel.

During the deployment of the tubular sleeve 1 caused by the dilatation of the balloon catheter 14, due to the attachment of the outer wall 5 on an inner wall of a hollow organ and the pressure transmitted from the balloon catheter to the inner wall 6, a compression pressure acts on the biocompatible substance arranged in the compartment 7. The compressive pressure can be more than 20 atm, whereby the microfibers are oriented approximately in the axial direction, i.e. in the direction of the sleeve longitudinal axis 2, and solidify in conjunction with the adhesive. In this way, a rigid structure is formed in the unfolded and unpleated final state of the tubular sleeve 1. Such a stiff structure, similar to the stents described at the outset, causes a support and maintains patency of the hollow organ.

Alternatively, the compartment 7 can be filled only with polylactide nano microfibers. The inner and/or the outer wall 5, 6 of the sleeve can then have microperforations, i.e., the outer wall 5 and the inner wall 6 have a porosity, the pores formed in the inner wall 6 and in the outer wall 5 having a maximum diameter smaller 100 μm, or less than 80 μm, or less than 60 μm, or less than 40 μm, or less than 30 μm, or less than 10 μm, and preferably less than 20 μm.

In this way, during the deployment and unfolding of the tubular sleeve 1, body fluid, in particular blood plasma, can enter the compartment 7. The entry of body fluid into the compartment 7 can be amplified by inflating and deflating the balloon catheter several times so that the outer wall 5 and the inner wall 6 of the sleeve 1 are repeatedly in direct blood contact. The inflowing plasma can have a similar effect to a synthetic adhesive because of its protein and fibrinogen content. In this way, the tubular sleeve 1 also undergoes a mechanical stabilization in its unfolded state.

According to a preferred embodiment, the sleeve is formed from a non-woven structure, wherein micro-compartments are formed between the individual fibers. The micro-porosity and micro-compartmentation of the fibers or of such a sleeve results in a passive suction effect of blood plasma after implantation in the blood vessel. Furthermore, the nonwoven is doped with calcium chloride salt, as a result of which fibrin polymerization is induced.

Figure 5:
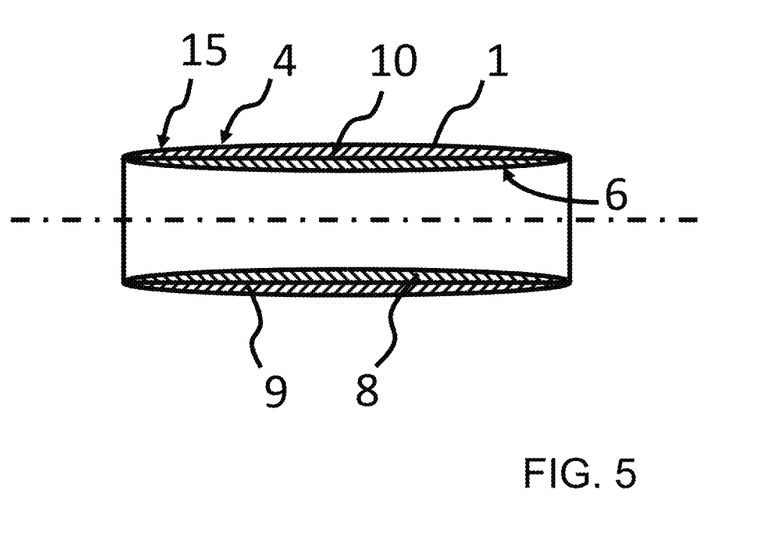
FIG. 5 shows a further embodiment of a sleeve according to the invention in a sectional side view.
Figure 6:
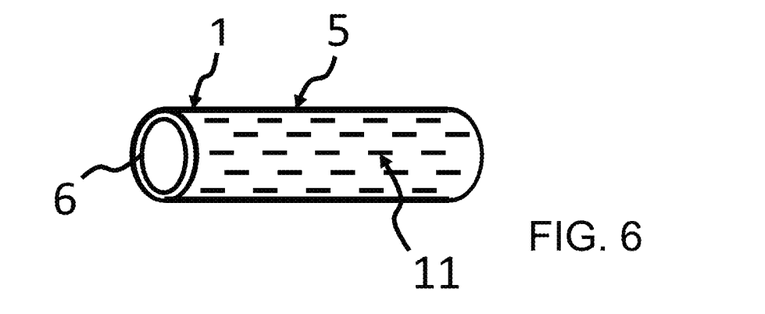
FIG. 6 shows an intermediate wall of the sleeve shown in FIG. 5 in a perspective view.
Figure 9:
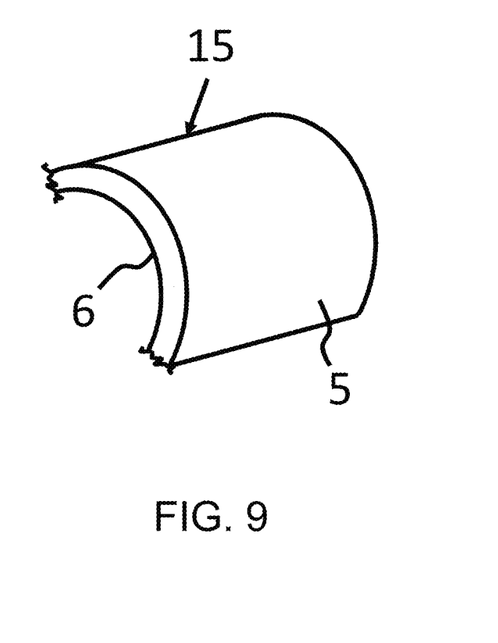
FIG. 9 shows a perspective detail view of the circumferential wall of the sleeve shown in FIG. 2.

According to an embodiment of the present invention, the tubular sleeve 1 has at least two compartments, in particular an inner compartment 8 and an outer compartment 9 (FIGS. 5, 6 and 9).

Unless otherwise described, this embodiment substantially corresponds to the second embodiment of the present invention.

Such a tubular sleeve 1 has an intermediate wall 10 between the outer wall 5 and the inner wall 6, which also extends in the longitudinal direction of the sleeve 2. The outer wall 5, the intermediate wall 10 and the inner wall 6 are each formed from a film of one of the above-described materials. The end regions or the front faces of the films are tightly joined together, for example by means of welding.

Accordingly, a tubular sleeve 1 according to this embodiment forms the outer compartment 9 between the outer wall 5 and the intermediate wall 10 and the inner compartment 8 between the intermediate wall 10 and the inner wall 6.

The inner compartment 8 and the outer compartment 9 extend coaxially with respect to the longitudinal axis 2 of the sleeve. PLA fibers or a PLA powder are arranged in the outer compartment 9. In the inner compartment 8, a crosslinking agent is present in liquid form.

In this case, it can be provided that the intermediate wall 10 has a smaller thickness and a smaller deployment diameter than the outer wall 5 and the inner wall 6.

In addition, the intermediate wall 10 can have predetermined tear lines in radial, approximately equal spacing from one another and distributed over the entire circumference in the longitudinal direction 2 of the sleeve (FIG. 6), which allow a defined or directed tearing of the intermediate wall. Preferably, these predetermined tear lines 11 have a length of 200 μm to 1000 μm.

When the tubular sleeve 1 is unfolded and unpleated, it is provided that the intermediate wall 10 tears along the desired predetermined breaking points or the perforated notches. The cracking is also favored by the fact that cracks in the longitudinal direction arise in a cylinder under internal pressure, since the tangential wall tension (transverse to the longitudinal direction) in the intermediate wall 10 is twice as high as in the longitudinal direction 2.

In this way, a connection between the inner compartment 8 and the outer compartment 9 is provided in such a way that the two substances contained therein are mixed with one another. The crosslinking agent or the binding agent arranged in the inner compartment 8 can, for example, be based on cyanacrylate, such as N-butyl-2-cyanoacrylate. In the outer compartment 9, polylactide (PLA) is preferably arranged as nanopowder or as micro-nanofibers. By contacting the crosslinking agent with the powdery or fibrous PLA, a polymerization reaction takes place, which leads to a mechanical consolidation of the sleeve content. This mechanical solidification of the deployed (unfolded) sleeve 1 prevents collapse into the pleated and folded state.

In addition, the cohesion of the outer wall 5, the intermediate wall 10 and the inner wall 6 during the pleating, the folding, the unfolding and unpleating process can be supported by connection points or connection lines between the walls 5, 10, 6, for example, by laser welding.

Figure 7:
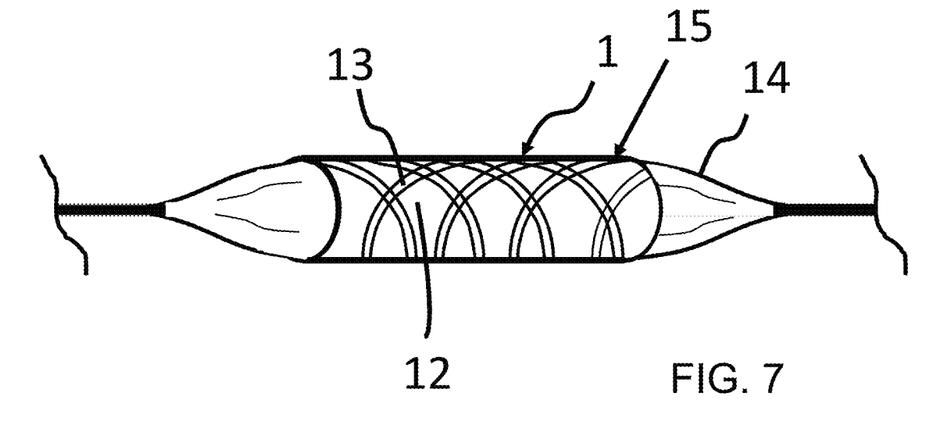
FIG. 7 shows a further embodiment of the sleeve according to the invention on a balloon catheter with an inflated balloon in a perspective view from the side.
Figure 8:
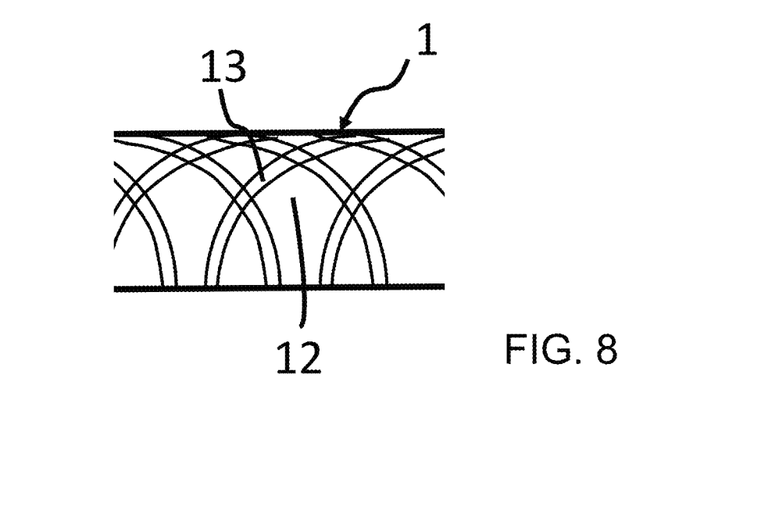
FIG. 8 is a detailed view of the circumferential wall of the sleeve shown in FIG. 7.

According to a further embodiment of the present invention, which essentially corresponds to the second embodiment, the sleeve 1 can comprise an outer wall 5 and an inner wall 6 (FIGS. 7 and 8).

In this case, it is provided that the outer wall 5 and the inner wall 6 are arranged transversely or obliquely to the longitudinal direction with one another, for example, by means of laser welding, that channels 13, similar to a diamond pattern, extend helically along the entire wall of the sleeve 1, consisting of outer wall 5 and inner wall 6. As an alternative to the laser welding process, a hot-embossing process on a metal core is also conceivable for producing the channels 13, generating the strut or channel patterns are by corresponding projections.

The spiral-shaped cavities or channels 13 may be filled with a drying substance such as, for example, a polylactide nanopowder, the interspaces 12 between the struts being filled with a crosslinking or binding agent, for example, on a cyanoacrylate basis.

Both such channels 13 and the interspaces 12 are (sub-) compartments for the purposes of the present invention.

When the tubular sleeve 1 is unfolded and unpleated, the pressure resulting from the expansion of the balloon catheter 14 causes the intermediate spaces 12 filled with liquid cross-linking agent to be pressed flattened between the channels 13 and mechanically pressing the crosslinking agent towards the channels 13, until the walls of the channels 13 tear. In this way, the binder and the nanopowder are mixed.

The foils, from which the inner wall 6 and the outer wall 5 are formed, maintain a balloon catheter pressure up to about 25 atm without tearing. The welds of the channels 13 have very low mechanical strength. In the initial state, pleating and folding as well as application to a balloon catheter is possible in such a way that the compartments are reliably separated from each other. However, with increasing balloon pressure, they break, while the inner and outer sheets remain intact.

In all the above-described embodiments, which comprise both a liquid component in the form of a binder or crosslinking agent, as well as a solid component in the form of a powder or of fibers, it is in principle also possible to deliver the liquid component from the outside, for example, by feeding them via an additional channel of a balloon catheter, which allows a complete feeding of the compartment. If desired, an overflow can also be provided, which allows excess liquid to be discharged from the corresponding compartment.

Alternatively, the liquid required for the swelling process can also be provided by contact with blood plasma, whereby the contact with blood can take place via a porous or permeable outer wall or membrane with corresponding porosity or via a non-woven structure. For this purpose, the definition of the closed circumferential wall explained at the outset applies.

The solidification of the tubular sleeve 1 according to the invention can be effected in that the two components described above, such as, for example, powders or fibers, and the binders or crosslinking agents can be mechanically combined, that is, by penetration or tearing of intermediate walls between compartments or sub-compartments. Furthermore, an active injection or a passive suction of a liquid crosslinking agent is also possible.

According to a further embodiment of the passive sucking-in of a liquid crosslinking agent, this crosslinking agent can also be a blood plasma, wherein the microporous, micro-compartmented sleeve material is preferably a non-woven of polylactide fibers doped with calcium chloride salt to initiate a fibrin polymerization reaction.

A mechanical and thermal action of ultrasound is also conceivable. For example, it is possible to introduce an ultrasound probe together with the balloon catheter to the implantation site.

Alternatively, an optical-thermal combination is also implemented by integrating a laser device into the balloon catheter to facilitate exposure to UV light, for example, for laser sintering of PLA powder.

Furthermore, a high-frequency probe device can also be provided, which is likewise arranged in the balloon catheter and acts on the tubular sleeve by means of thermal energy.

A chemical stabilization by so-called click chemistry, such as the thiol-ene reaction, for example, by photopolymerization and integration of a UV laser device into the balloon catheter is possible.

All the embodiments described above can provide that a medical active substance is applied to the external wall 5 of the tubular sleeve 1, or the external wall 5 is doped with such a medical active substance. A medical active substance within the scope of the present invention is understood to be an antiproliferative and/or a healing-promoting substance such as fibringel. Such medicinal active substances can also be mixed with autologous cells of the patient, wherein prevention of blood contact and thrombus formation during the transport of the sheath to the implantation site can take place by means of an outer protective sheath. Such an outer protective sheath can be removed at the implantation site by retraction thereof. Alternatively, it is also possible to provide an external safety net or a safety sleeve which ruptures during unfolding and deployment, since it has a smaller deployment diameter than the tubular sleeve 1.

The stability of the folding and pleating of the sleeve 1 during transport or insertion into the hollow organ can be supported by an adhesive surface treatment of the outer wall of the sleeve.

On the inside, the inner wall 6 can also be provided with an antithrombogenic substance, e.g. heparin, and/or an active substance, which promotes endothelial cell coating.

Furthermore, a preparation or a priming of the inner and outer walls of the sleeve can be carried out immediately before the implantation in that the surfaces are filled with patient-specific substances of the patient, for example, whole blood, plasma, serum or cells.

In addition, wetting of the inner and outer walls of the sleeve during the implantation procedure can take place in situ with bioactive substances or body-borne substances of the recipient patient by delivering these via feed channels, these being part of the balloon catheter and being connected to the tubular sleeve 1 such that they lead to the inside or to the outside of the sleeve.

The walls, respectively their properties for the adhesion and storage of active substances, can be improved by surface structuring, gel film deposition or corresponding pores.

According to a method for the manufacture of a system for the atraumatic treatment of hollow organs according to the invention, it is provided that a balloon film of a balloon catheter is pleated together and folded together with the tubular sleeve in one working step.

Various embodiments of a circumferential wall 15 of a sleeve 1 according to the invention are described below.

Figure 10:
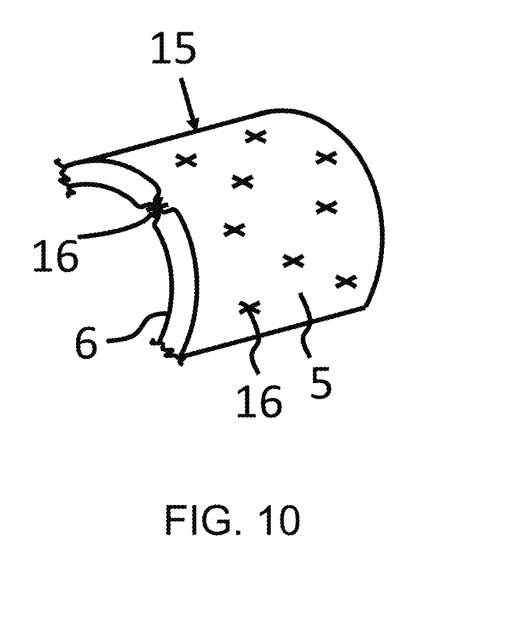
FIG. 10 shows a perspective detail view of the circumferential wall of a further exemplary embodiment of a circumferential wall, in which the inner and outer walls are connected to one another via connecting points.

Connecting points 16 can be formed between the inner and outer walls 6, 5, which are distributed approximately uniformly over the entire outer wall 15 (FIG. 10).

Preferably, the inner and outer walls 6, 5 are connected directly in the region of the connecting points 16 in such a way that inner and outer walls 6, 5 contact one another in the region of the connecting points. The connecting points can be provided, for example, by welding or adhesive bonds. Within the scope of the present invention, the connecting points can also be provided as struts (not shown) extending between the inner and outer walls, which are preferably formed from the same material as the sleeve.

Instead of or in addition to the connection points 16, it is also possible to provide continuous or section-shaped connecting lines (not shown).

Figure 11:
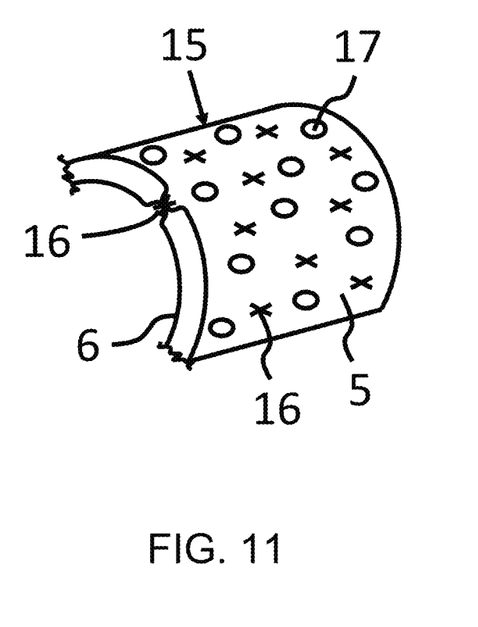
FIG. 11 is a perspective detail view of the circumferential wall of a further exemplary embodiment of a circumferential wall, in which the inner and outer walls are connected to one another via connecting points, wherein at least in the outer wall openings or pores are provided.

According to a further exemplary embodiment of the circumferential wall 15, in addition to the connecting points 16, openings or pores 17 are provided, which are distributed uniformly over the outer wall of the circumferential wall (FIG. 11). The pores 17 formed in the sleeve have a diameter in the range between 1 µm and 100 µm, or between 5 µm and 80 µm, or between 5 µm and 60 µm, or between 5 µm and 40 µm, or between 5 µm and 30 µm or between 5 µm and 10 µm, and preferably between 5 µm and 20 µm.

Figure 12:
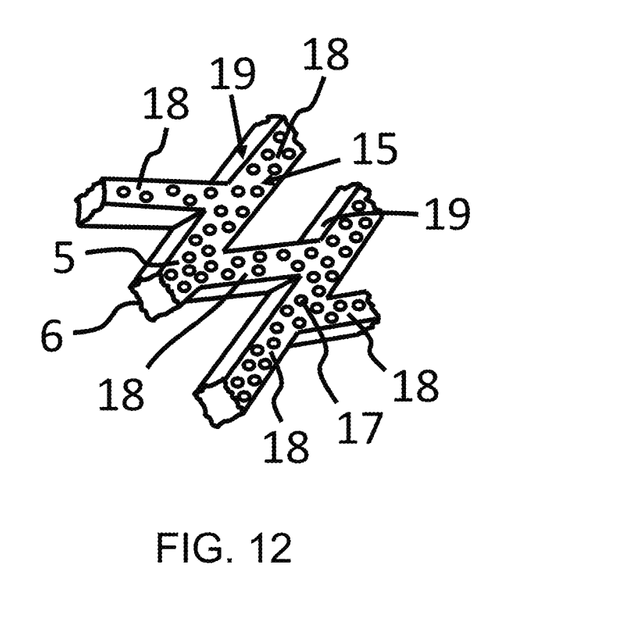
FIG. 12 shows a perspective detail view of the circumferential wall of a further exemplary embodiment of a strut-lattice-like circumferential wall, wherein at least in the outer wall openings or pores are provided.
Figure 13:
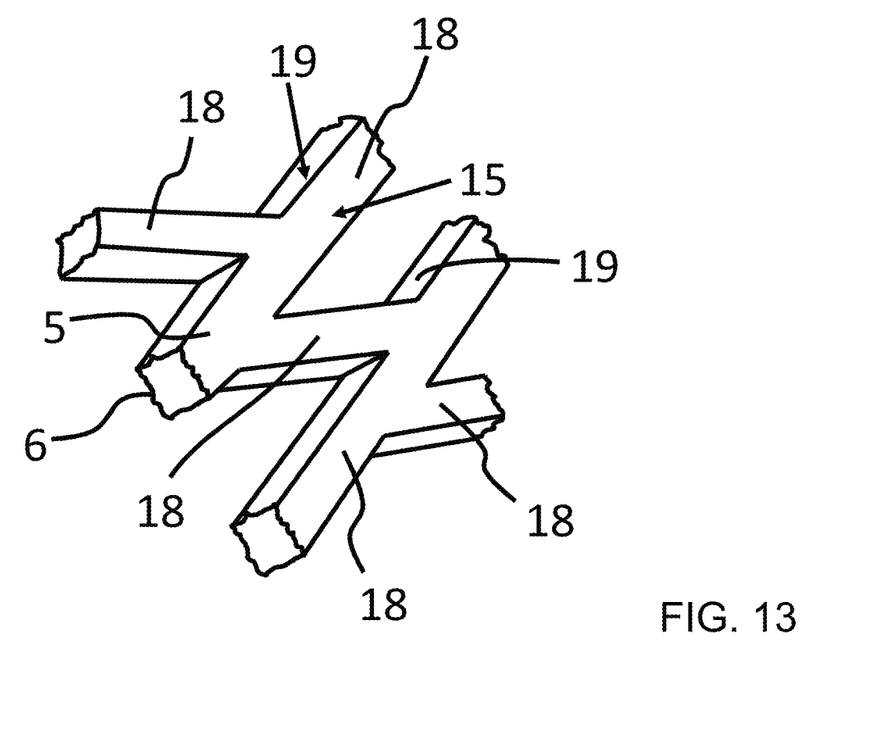
FIG. 13 is a perspective detail view of the circumferential wall of a further exemplary embodiment of a strut-lattice-like circumferential wall.

According to a further exemplary embodiment, the entire circumferential wall 15 can be designed as a lattice-like structure (FIGS. 12 and 13). The individual struts 18 of the lattice structure, in particular the outer, inner and also possibly existing side walls 19, then define the compartment of the sleeve.

In this exemplary embodiment, the lattice-configurated struts 18 can also have the openings, connection points, partition walls or webs already described above such that several compartments 7 are formed in the lattice structure.

Figure 14:
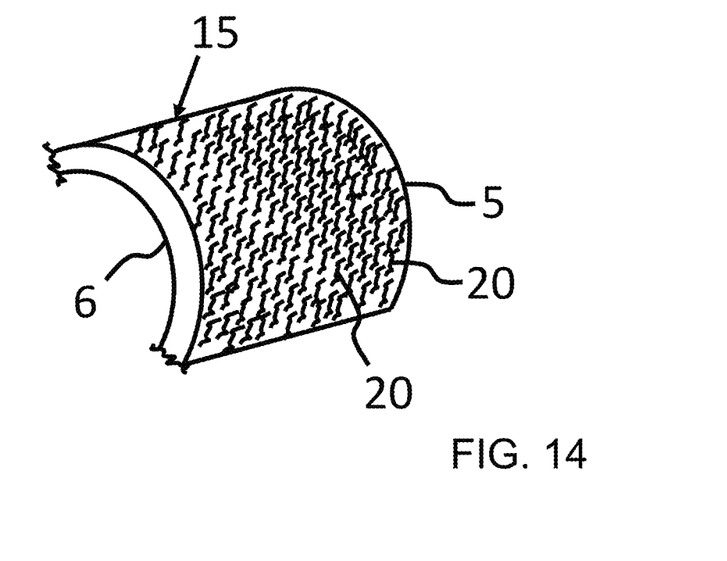
FIG. 14 shows a perspective detail view of the circumferential wall of a further exemplary embodiment of a circumferential wall, wherein pins are provided on the circumferential wall on the outer side in the direction of a hollow organ for the binding of a medical active substance.

According to a further exemplary embodiment, the outer wall of the circumferential wall 15 provide extending pins 20 and microfibrils, which extend in the direction of the hollow organ, forming a microstructure (FIG. 14). Such a microstructure is particularly suitable for binding a hydrogel and/or a medical active substance.

Figure 15:
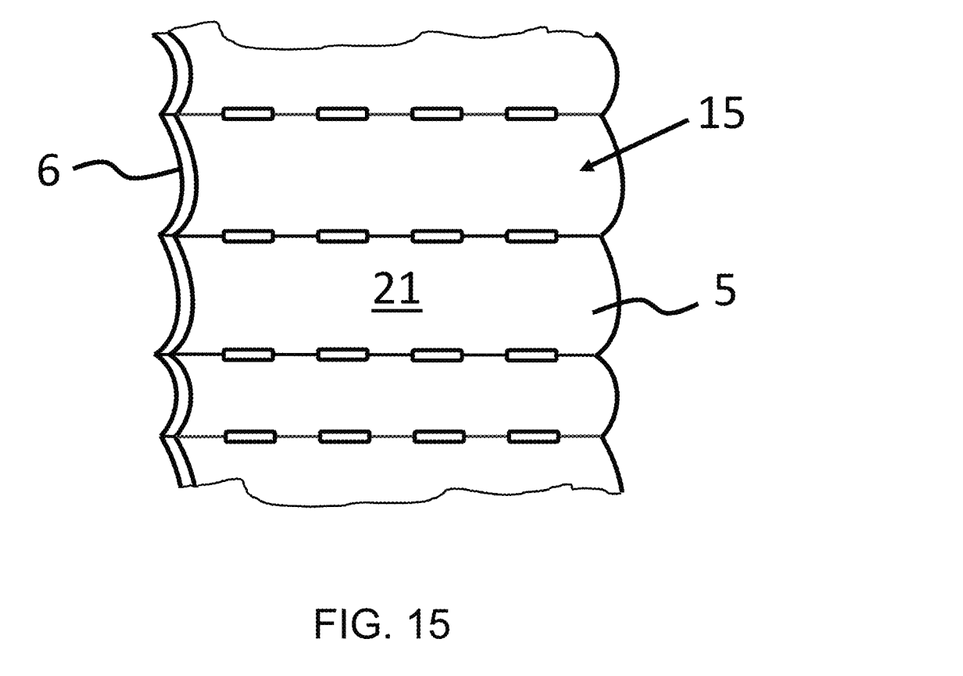
FIG. 15 shows a perspective detail view of the circumferential wall of a further exemplary embodiment of a lattice-like circumferential wall, According to a first exemplary embodiment, a tubular sleeve 1 for the atraumatic treatment of hollow organs is formed cylindrically from a single wall (FIGS. 1 to 3).

According to a further exemplary embodiment, the circumferential wall is formed from casing wall sections which extend in the longitudinal direction and are connected to each other transversely to the longitudinal direction or in the radial direction in a joint-like manner (FIG. 15). Such circumferential wall sections 21, like the above-described embodiments, have corresponding components 7.

According to an alternative embodiment of the present invention, the entire tubular sleeve is formed from a nonwoven fabric (not shown). Accordingly, both the outer and inner walls 5, 6 are formed by the nonwoven fabric. A nonwoven fabric is also provided in the region between the outer and inner walls 5, 6. Accordingly, the entire circumferential wall 15 of the tubular sleeve can be designed as an integral nonwoven fabric structure. The compartments 7 are then provided as micro-compartments in the region between the individual fibers of the nonwoven fabric. A filler can also be arranged, embedded or bound in these micro-compartments 7.

Further advantages of individual embodiments as well as exemplary advantageous embodiments are described below.

All embodiments of the present invention can have pores 17 in the inner and/or outer wall 6, 5.

All embodiments of the present invention may have pins on the inner and/or outer wall 6, 5, which then extend radially towards the axis of the device or radially outwards.

All embodiments of the present invention may comprise webs, connecting lines, points, walls, wall sections or the like, between the inner and outer walls 6, 5 and/or between these and one or more coaxial or radial intermediate walls.

The compartment 7 or the compartments enable a good spatial configuration for a depot of an active substance. Such an active substance depot allows, for example, a storage of an active agent-doped gel.

A preferred embodiment comprises a pleated sleeve (in the form of a film) of PLA with a wall thickness in the range between 20-50 μm, the outer surface being coated with a hydrogel and/or an adhesive. The inner surface area can be chemically biofunctionalized or coated with an active agent.

A further preferred embodiment comprises an inner thick film having a wall thickness in the range between 20-40 μm and of an outer thin film with a wall thickness in the range between 5-10 μm, the latter having multiple pores. In the compartment between the two films is a layer of active-agent-loaded hydrogel, which is held in the form of a depot in situ, but the active ingredient can be released gradually over the pores on the outer surface.

Such a structure can be expanded as desired, for example with a further porous film as an intermediate wall, with a second, other active substance depot. Or with a division of the tube-shaped or sleeve-shaped compartment into a plurality of sub-compartments, which may result in a larger number of micro-compartments.

Furthermore, the film forming the inner wall can have a thickness of, for example, 90 μm. In this way, the inner wall would form a stent body with a sufficient radial supporting force, which can support a vessel lumen, which, for example, threatens to collapse after balloon dilatation. In order to improve the folding of the relatively thick film, the film may have longitudinal slots which correspond to the folding folds (FIG. 15).

Accordingly, the inner and/or intermediate and/or outer wall of a sleeve according to the invention can have a predetermined radial supporting force, which then determines the radial supporting force of the sleeve. E.g. the intermediate wall can be relatively thick, and in compartments between the intermediate wall and the outer and inner walls, an active substance filled compartment is formed, so that the intermediate wall determines the radial supporting force. The same is possible with a thicker outer or inner wall with or without intermediate wall.

LIST OF REFERENCES

1 Tubular sleeve
2 Longitudinal axis of the sleeve
3 Outer wall
4 Hydrogel layer
5 Outer wall
6 Inside wall
7 Compartment
8 Inner compartment
9 Outer compartment
10 Intermediate wall
11 Predetermined tear lines
12 Interstices
13 Channels
14 Balloon catheter
15 Circumferential wall
16 Connection point
17 Connection line
18 Strut
19 Side wall
20 Pin
21 Circumferential wall section

The invention claimed is:

1. A tube-shaped sleeve for atraumatic treatment of hollow organs, wherein the sleeve being folded to a smaller diameter in an initial state, and unfolded to its maximum diameter in an end state, to attach to an inner wall of a hollow organ, wherein the sleeve is formed from an outer wall and an inner wall, which are concentric to each other, and wherein the outer wall and the inner wall are connected to one another on end faces so tightly that in a region between the outer wall and the inner wall an approximately tubular-shaped compartment is formed, and the folding of the sleeve is carried out as a pleating, where the pleats are orientated along a longitudinal axis of the sleeve, wherein both the outer wall and the inner wall of the sleeve and a first filler arranged in the compartment between the outer and inner wall are made of a textile structure, which is continuously made of nonwoven fibers, wherein interspaces between fibers in the compartment form micro-compartments, and wherein a circumferential wall of the sleeve has adhesive properties and/or is provided with a coating so that the outer surface adheres to an inner wall of the hollow organ during and/or after unfolding, and wherein the sleeve is provided with a bioactive substance, and wherein the sleeve is made of one or more biodegradable polymers.

2. A tube-shaped sleeve according to claim 1, wherein the coating of the sleeve is an adhesive hydrogel.

3. A tube-shaped sleeve according to claim 1, wherein the bioactive substance is an antiproliferative.

4. A tube-shaped sleeve according to claim 1, wherein the circumferential wall of the sleeve is lattice-like.

5. A tube-shaped sleeve according to claim 1, wherein the circumferential wall of the tubular sleeve is substantially closed, wherein the inner and/or outer wall have a porosity, and the pores formed in the sleeve having a maximum diameter of less than 100 μm.

6. A tube-shaped sleeve according to claim 1, wherein thicknesses of each of the inner and outer walls account for approximately 20 μm.

7. A tube-shaped sleeve according to claim 1, wherein the sleeve is cylindrical, conical or constricting.

8. A tube-shaped sleeve according to claim 1, wherein a second filler or a crosslinking agent or a binder or an adhesive is arranged in the micro-compartments of the nonwoven fibers.

9. A tube-shaped sleeve according to claim 1, wherein the sleeve is provided with a healing-promoting biological substance, at which the substance is optionally mixed with autologous cells of a patient.

10. A tube-shaped sleeve according to claim 9, wherein the healing-promoting biological substance comprises fibrin gel.

11. A tube-shaped sleeve according to claim 1, wherein in the sleeve, in the unfolded state, takes place in situ polymerization of at least two components in the micro-compartments.

12. A tube-shaped sleeve according to claim 1, wherein fibrin polymerization is effected by a passive suction of a liquid crosslinking agent, comprising a body fluid, and the sleeve is doped with calcium chloride salt to initiate the fibrin polymerization.

13. A tube-shaped sleeve according to claim 1, characterized in a doping of an inner surface of the sleeve with an antithrombogenic substance and/or an active substance, which promotes endothelial cell coating.

14. A tube-shaped sleeve according to claim 13, wherein the antithrombogenic substance comprises heparin.

15. A tube-shaped sleeve according to claim 1, wherein the sleeve comprises polylactic acid (PLA).

16. System for the atraumatic treatment of hollow organs comprising a tube-shaped sleeve according to claim 1, and a balloon catheter, wherein the wherein pleating and folding of the balloon film of a balloon catheter and the tube-shaped sleeve, which is coaxially adjoining on the outside of the balloon film, is done in one working step.

17. System for the atraumatic treatment of hollow organs comprising a tube-shaped sleeve according to claim 16.

* * * * *